United States Patent
Clancy et al.

(10) Patent No.: US 7,858,073 B2
(45) Date of Patent: Dec. 28, 2010

(54) ORAL KILLED VACCINES AND METHOD FOR PROVIDING SAME

(75) Inventors: Robert Clancy, Newcastle (AU); Phillip Comans, Faulconbridge (AU); Gerald Pang, Elizabeth Bay (AU)

(73) Assignee: Hunter Technology Limited, French Forest (AU)

( * ) Notice: Subject to any disclaimer, the term of this patent is extended or adjusted under 35 U.S.C. 154(b) by 0 days.

(21) Appl. No.: 11/573,889

(22) PCT Filed: Aug. 17, 20054

(86) PCT No.: PCT/AU2005/001230

§ 371 (c)(1),
(2), (4) Date: Aug. 28, 2007

(87) PCT Pub. No.: WO2006/017895

PCT Pub. Date: Feb. 23, 2006

(65) Prior Publication Data

US 2008/0112979 A1 May 15, 2008

(30) Foreign Application Priority Data

Aug. 17, 2004 (AU) .............................. 2004904679

(51) Int. Cl.
*A61K 49/00* (2006.01)
*A61K 39/02* (2006.01)
*A61K 39/108* (2006.01)

(52) U.S. Cl. ...................... 424/9.2; 424/9.1; 424/184.1; 424/234.1; 424/243.1; 424/244.1; 424/256.1; 424/257.1; 424/260.1; 424/263.1

(58) Field of Classification Search .................. 424/9.1, 424/9.2, 184.1, 234.1, 243.1, 244.1, 256.1, 424/257.1, 260.1, 263.1
See application file for complete search history.

(56) References Cited

U.S. PATENT DOCUMENTS

2003/0039667 A1  2/2003  Jira et al.

FOREIGN PATENT DOCUMENTS

| WO | WO-99/38529 | 8/1999 |
| WO | WO-01/87332 | 11/2001 |
| WO | WO0187332 | 11/2001 |
| WO | WO2004035007 | 4/2004 |

OTHER PUBLICATIONS

Gilbert et al., "Sieve analysis—methods for assessing from vaccine trial data how vaccine efficacy varies with genotypic and phenotypic pathogen variation", Journal of Clinical Epidemiology, Jan. 2001, 68-85(18), vol. 54(1).

Hamers et al., "Virus neutralising antibodies against 22 bovine viral diarrhoea virus isolates in vaccinated calves", Vet J., Jan. 2002; 61-7; vol. 163(1).

Hirano et al., "Intranasal immunization with a lipooligosaccharide-based conjugate vaccine from nontypeable Haemophilus influenzae enhances bacterial clearance in mouse nasopharynx", FEMS Immunology & Medical Microbiology, 2003, 1-10, vol. 35 (1).

*Primary Examiner*—Rodney P. Swartz
(74) *Attorney, Agent, or Firm*—Kaplan Gilman & Pergament LLP (57) ABSTRACT

There is described a method for selecting microbial isolates for use in oral killed vaccines against abnormal microbial colonization of mucosal surfaces by the microbes. The method comprises evaluating capacity of a plurality of different isolates of a microbe to activate antigen responsive cells to provide activation data for each microbial isolate, and the effectiveness of the isolates in reducing infection of a mucosal surface by the microbe to provide clearance data for each microbial isolate. An isolate, the activation data and clearance data for which correlate and is optimal for generating mucosal immunity against the microbe compared to the, or each, other of the isolates, or an isolate the activation data for which is optimal and a further isolate the clearance data for which is optimal, compared to the, or each, other of the isolates, respectively, is then selected for use in the vaccine. There is also described a method for providing an oral killed vaccine against abnormal microbial colonization of a mucosal surface, comprising evaluating the capacity of a plurality of different isolates of a microbe to induce expression of IL-10 and IL-12 in antigen responsive cells. At least one isolate is selected that induces optimal expression of IL-12 relative to IL-10 compared to the, or each, other of the isolates, respectively, for use in the vaccine.

42 Claims, 1 Drawing Sheet

ORAL KILLED VACCINES AND METHOD FOR PROVIDING SAME

FIELD OF THE INVENTION

The present invention relates to a method for selecting unicellular microbial isolate(s) for use in oral killed vaccines, for inducing a protective mucosal immune response against abnormal colonization of a mucosal surface by the microbe. Oral killed vaccines for the prophylaxis or treatment of such infections are also provided.

BACKGROUND OF THE INVENTION

Anti-bacterial vaccines are known in the art and examples include *Haemophilus influenzae* B vaccine which consists of bacterial polysaccharide conjugated with tetanus toxoid protein. Killed bacterial vaccines for the prophylaxis or treatment of enteric infections have also been known for some time and a killed bacterial vaccine for typhoid fever is commercially available. These vaccines are predominantly if not exclusively administered by injection and serve as "classic" vaccines in that they aim to stimulate a systemic antibody response to provide protection against disease.

Antigen administered orally is processed by gut-associated lymphoid tissue (GALT) differently from systemic lymphoid tissue. Teleologically, this can be understood in terms of mucosal physiologically where environmental "antigen" needs to be excluded but not at the cost of damaging mucosal "inflammation". A powerful suppression mechanism therefore exists, to minimize potentially damaging immune responses to such antigen. This concept was originally identified as "split tolerance" where a systemic immune response (ie. mediated by the generation of antibody) was associated with the failure to detect a mucosal antibody response (tolerance). Research using orally administered killed influenza virus shows that an antibody response is stimulated over a narrow range of antigen dose. This immunization "zone" is flanked by low and high "zone" tolerance. The same concept applies to cellular immunity though the zone in which T-lymphocyte-mediated responses may be stimulated appears to be marginally wider with protection occurring without an antibody response. The outcome of antigen interaction with GALT is the selective migration of B and T-lymphocytes to distant mucosal sites of infection where they mediate protection.

An oral killed bacterial vaccine against infection by non-typeable *Haemophilus influenzae* (NTHi) is also known in the art. NTHi is the bacteria most commonly linked with nasal and bronchus colonization in subjects with chronic lung disease, and has been linked to acute episodes of bronchitis in these subjects. A significant factor in the generation of acute bronchitis in such subjects is the uncontrolled and inappropriate migration of neutrophils into the bronchus lumen in response to the colonizing bacteria. The accumulation of neutrophil-laden fluid within the bronchi results in purulent sputum. The use of the oral NTHi killed bacterial vaccine has been shown to protect against purulent sputum production, high levels of bacterial colonization of the airways and environmental spread of the bacteria as assessed by acquisition of infection by bystander subjects. The NTHi vaccine stimulates the common mucosal system following activation of GALT and more specifically, Peyer's patches in the intestines.

Oral non-adjuvenated monobacterial vaccines comprising killed bacteria for providing mucosal immunity particularly in patients with long term chronic lung disease are described in international patent application No. PCT/AU86/00071. Specifically, the application indicates that the immunization efficacy of the vaccine arises from the absence of adjuvant, which would normally be included in such vaccine formulations to promote an immune response. The generation of the immune response in the absence of the adjuvant was reasoned to be due to the response elicited by the killed bacteria being insufficient to trigger dominant suppressor T-cell populations in the lungs of the patients evaluated.

SUMMARY OF THE INVENTION

Broadly stated, the present invention relates to the provision of oral killed vaccines for protecting against abnormal microbial colonization and stems from the recognition that there is a marked variation in the clearance of such infections elicited by oral killed vaccines in an outbred population, reflecting the genetic variation in the population. The variation in mucosal immunity associated with the use of prior art oral killed bacterial vaccines is believed to arise from the use of less optimal or randomly chosen microbial isolates in the vaccines, due to the failure to recognize the significant variability in the capacity of different isolates of a microbe to activate antigen-presenting cells and T-lymphocytes. Given the observed variability, the selection of the isolate(s) is critical for optimizing the degree of activation of the common mucosal system in different individuals in an outbred population. Methodology provided in one or more embodiments of the present invention enables the selection of isolate(s) for optimizing oral killed vaccines.

More particularly, in one aspect of the present invention there is provided a method for selecting a microbial isolate for an oral killed vaccine against abnormal microbial colonization of a mucosal surface, the method comprising:

evaluating capacity of a plurality of different isolates of a unicellular microbe to activate antigen responsive cells to provide activation data for each microbial isolate;

evaluating effectiveness of the isolates in reducing infection of a mucosal surface by the microbe to provide clearance data for each microbial isolate; and selecting an isolate from the microbial isolates, the activation data and clearance data for which correlate and is optimal for generating mucosal immunity against the microbe compared to the, or each, other of the isolates, or an isolate the activation data for which is optimal and a further isolate the clearance data for which is optimal, compared to the, or each, other of the isolates, respectively, for use in formulating the vaccine.

In another aspect of the present invention there is a method for providing an oral killed vaccine against abnormal microbial colonization of a mucosal surface, the method comprising:

evaluating capacity of a plurality of different isolates of a unicellular microbe to activate antigen responsive cells to provide activation data for each microbial isolate;

evaluating effectiveness of the isolates in reducing infection of a mucosal surface by the microbe to provide clearance data for each microbial isolate;

selecting an isolate from the plurality of isolates, the activation data and clearance data for which correlate and is optimal for generating mucosal immunity against the microbe compared to the, or each, other of the isolates, or an isolate the activation data for which is optimal and a further isolate the clearance data for which is optimal, compared to the, or each, other of the microbial isolates, respectively, for use in formulating the vaccine; and formulating the vaccine using the selected isolate or isolates.

Typically, an isolate for which both the activation data and the clearance data is optimal compared to the other of the isolates will be selected.

Preferably, the mucosal immunity will comprise predominantly a cellular immune response.

Preferably, the isolates utilized for providing the activation and clearance data will be killed isolates of the microbe. However, the invention is not limited thereto and the activation and clearance data may be obtained from live isolates and the selected isolate(s) subsequently killed for use in the vaccine.

The antigen responsive cells activated by the isolate(s) will normally comprise one or both of antigen presenting cells and T-lymphocytes and preferably, will comprise both types of cells. The antigen presenting cells will typically comprise macrophages. Most preferably, the T-lymphocytes will be Th1 cells. The activation of the antigen responsive cells is to be taken in its broadest sense to encompass direct and/or indirect activation by the isolate(s). By "direct" activation is meant the isolate(s) activate at least some of the antigen responsive cells by contact with the cells such as when a microbial isolate is bound or phagocytosed by them. By "indirect" activation is meant at least some of the antigen responsive cells are activated by interaction with the cells such as macrophages that have contacted the isolate or for instance, by cytokine(s) or other chemical messenger(s) the release of which has been elicited or induced by the isolate(s), or by substances such as toxins or antigens secreted by the isolate(s), or a combination of the foregoing possibilities.

The level of activation of the antigen responsive cells can be evaluated by measuring one or more parameters associated with activation of the cells. Preferably, the capacity of the isolate(s) to activate both antigen presenting cells and T-lymphocytes will be evaluated. In particularly preferred embodiments, the activation of the antigen responsive cells achieved by each isolate will be evaluated by measuring at least one parameter indicative of the level of activation of the antigen presenting cells and at least one other parameter indicative of the level of activation of the T-lymphocytes. Most preferably, isolate(s) the activation data for which is optimal for activating both antigen presenting cells and T-lymphocytes compared to the other isolate(s) tested will be selected for use in the preparation of the oral killed vaccine.

Preferably, an isolate the activation data for which is indicative of the capacity of the isolate to elicit a cytokine response characterized by an IL-10:IL-12 ratio of about 30 or less will be selected for use in formulating the oral killed vaccine.

Hence, in another aspect of the present invention there is provided a method for selecting a microbial isolate for an oral killed vaccine against abnormal microbial colonization of a mucosal surface, the method comprising:

evaluating capacity of a plurality of different isolates of a unicellular microbe to induce expression of IL-10 and IL-12 in antigen responsive cells; and selecting at least one isolate from the microbial isolates, that induces optimal expression of IL-12 relative to IL-10 compared to the, or each, other of the isolates, respectively, for use in formulating the vaccine.

In still another aspect of the present invention there is provided a method for providing an oral killed vaccine against abnormal microbial colonization of a mucosal surface, the method comprising:

evaluating capacity of a plurality of different isolates of a unicellular microbe to induce expression of IL-10 and IL-12 in antigen responsive cells;

selecting at least one isolate from the microbial isolates, that induces optimal expression of IL-12 relative to IL-10 compared to the, or each, other of the isolates, respectively, for use in formulating the vaccine; and formulating the vaccine using the isolate.

The unicellular microbe can be any such microbe having the capacity to colonize a mucosal surface of a mammal and may for instance be selected from the group consisting of bacteria, fungi and yeast. Typically, the microbe will be a bacteria and the vaccine will therefore be an oral killed bacterial vaccine. Preferably, the selected isolate(s) will be used in the vaccines of the invention as whole killed organisms. However, the invention is not limited to the use of whole killed organisms and vaccines may be provided comprising particulate matter derived from the outer cellular membrane of the selected isolate(s).

In yet another aspect, the present invention relates to an oral killed vaccine provided by a method of the invention.

A vaccine of the invention may be directed against infection of any mucosal site including chronic and acute such infections. The infection can be the result of transient exposure to a microbial pathogen which does not normally colonise the mucosal site or for instance, an opportunistic infection arising from microbial flora normally found at the site.

Accordingly, in another aspect, there is provided a method for the prophylaxis or treatment of an infection of a mucosal surface in a mammal by a unicellular microbe, the method comprising:

administering to the mammal an effective amount of an oral killed vaccine of the invention for generating mucosal immunity against the microbe.

The mammal may be any mammal treatable with an oral killed bacterial vaccine of the invention. For instance, the mammal may be a primate, a member of the rodent family such as a rat or mouse, or a member of the bovine, porcine, ovine or equine families. Preferable, however, the mammal will be a human being.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

All publications mentioned in this specification are herein incorporated by reference. Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed in Australia or elsewhere before the priority date of each claim of this application.

The features and advantages of the present invention will become further apparent from the following description of preferred embodiments.

DETAILED DESCRIPTION OF THE PREFERRED EMBODIMENTS

Vaccines embodied by the invention find particular application in the prophylaxis or treatment of lung and upper respiratory tract infections. However, the invention is not limited thereto and mucosal immunity resulting from activation of the common mucosal system may provide protection or treatment against infections at other mucosal sites of the body including infections of the oral, nasal, oropharyngeal, nasal pharyngeal, pharyngeal, digestive, vaginal, eye associated, and urinary mucosal surfaces. The vaccine may contain bacteria selected for instance from *Chlamydia* species, *Haemophilus* species, Non-typeable *Haemophilus* species, *Pseudomonas* species, *Streptococcus* species, *Staphylococcus* species, *E. coli* species, *Mycoplasma* species and *Helicobacter* species amongst others, or incorporate combinations of different species of bacteria or of other unicellular microbes. Microbes other than bacteria that may be used in oral killed vaccines according to the invention include *Candida* species such as *Candida albicans* and yeast species such as *Saccharomyces* species. Particularly preferred oral killed bacterial vaccines embodied by the invention are vaccines for the prophylaxis or treatment of mucosal infections by bacteria selected from the group consisting of Non-typeable *H. influenzae* (NTHi), *S. aureus*, *P. aeruginosa*, *S. pneumoniae* and combinations thereof.

While the primary application of a vaccine embodied by the invention is to generate mucosal immunity against the particular bacterial infection(s) for which the vaccine is provided, which may occur at various mucosal sites, the vaccine can also be used for the treatment or prophylaxis of diseases or conditions exacerbated by the infection(s).

*P. aeruginosa* for instance can colonise not only the respiratory tract but can also infect eye mucosa and the ear cavity. Non-typeable *H. influenzae* (NTHi) has also been implicated in a range of infectious conditions including otitis media and in the exacerbation of pneumonia and chronic bronchitis. Accordingly, a vaccine containing one or more killed NTHi isolates of this bacteria may be administered for the prophylaxis or treatment of those conditions. Similarly, vaccines of the invention comprising killed *H. influenzae, S. pneumoniae* or *P. aeruginosa* may be utilized in the prophylaxis or treatment of bronchitis or pneumonia, and acute infections in cystic fibrosis and chronic obstructive airways disease, sinus disease, compromised lung function and other lung and respiratory tract diseases and disorders. These vaccines also find particular application in the prophylaxis or treatment of superinfection by the corresponding bacteria following infection by *influenzae* virus or other virus, particularly in the elderly.

While it is preferable to use whole killed isolate(s) in vaccines of the invention, particulate cell surface matter comprising surface antigens of the isolate(s) may be utilized as well, or instead of, whole killed organisms. In a particularly preferred embodiment, the outer cellular membrane fraction of the organisms will be utilized. The particulate matter can be prepared by disrupting killed or viable selected isolate(s) by sonication or other suitable technique and if desired, separating the required fraction from other cellular components such as by centrifugation, filtration and/or other appropriate technique known in the art. Any suitable method which achieves the required level of cellular disruption may be employed including sonication or dissolution utilizng appropriate surfactants and agitation. When sonication is employed, the isolate may be subjected to a number of sonication steps in order to obtain the desired degree of cellular disruption or generation of particulate matter of a desired size. The fraction of particulate matter utilized may be selected by comparing the response of antigen responsive cells to different fractions of the isolate(s) and selecting the fraction which maximizes the immune response by the cells.

To evaluate the capacity of a microbial isolate or particulate matter thereof to activate the antigen responsive cells, any parameter which is indicative of the level of activation of the cells may be evaluated. Particularly, preferred parameters include one or more of cellular proliferation, cell surface antigen expression, measurement of cell effector functions, and cytokine production.

Cellular proliferation and in particular, T-cell proliferation, may be conveniently evaluated by cell counts, $^3$H-thymidine uptake and/or MTT assays.

Cytokine expression may be measured directly by capture or sandwich enzyme linked immunosorbent assays (ELISA), or indirectly by cell growth assays in which the cytokine of interest acts as a growth factor or inhibitor. Similarly, cytokine expression may be evaluated by determining the level of expression of mRNA coding for the cytokine by employing reverse transcriptase polymerase chain reaction (RT-PCR) or by in-situ hybridization protocols utilizing single cells and specific oligonucleotides probes as is known in the art.

The protective immune response generated by the vaccine will typically be predominantly mediated by Th1 T-lymphocytes which differentiate from proliferating $CD4^+$ T-lymphocytes in the presence of IL-12 and IFN-$\gamma$. IL-12 is produced by antigen presenting cells in the early stages of activation. Th1 T-lymphocytes stimulate infected macrophages through secretion of IFN-$\gamma$ and interaction of the CD40 ligand expressed by Th1 cells with the CD40 receptor expressed by macrophages. More broadly, Th1 cells stimulate the antibacterial mechanisms of phagocytic cells (eg. neutrophils and macrophages) and release cytokines that attract such phagocytic cells to sites of infection. Besides IFN-$\gamma$, Th1 cells typically also secrete IL-12 and TNF-$\beta$.

While both Th1 and Th2 cells secrete IL-3, GM-CSF and for instance TNF-$\alpha$, the overall cytokine profiles for Th1 and Th2 cells are different. More particularly, activation of Th2 cells results predominantly in a humoral immune response characterized by the activation of B-lymphocytes and the generation of antibodies by the activated B cells, while Th1 cells mediate a predominantly non-antibody cellular immune response. Cytokines characteristic of Th2 cell driven immune response include IL-4, IL-5, IL-10, IL-13 and TGF-$\beta$. Hence, detection of the secretion of one or more of IL-12, IFN-$\gamma$, or other cytokines characteristic of activated antigen-presenting cells and Th1 committed $CD4^+$ T-lymphocytes, is useful in evaluating the capacity of a given microbial isolate to activate the common mucosal system. Preferably, the level of IL-12 secretion will be measured to provide an indication of the degree of activation of antigen presenting cells by the microbial isolate(s) being evaluated. Similarly, the level of IFN-$\gamma$ secretion will typically be measured to provide an indication of the level of T-lymphocytes activation achieved by the microbial isolate(s).

In particularly preferred embodiments, the activation data may comprise a ratio indicating expression IL-10 relative to IL-12. IL-10 inhibits the release of cytokines such as IL-12 by macrophages and so inhibits Th1 cell activation. The ratio is therefore indicative of the level of a Th1 lymphocyte response elicited by a microbial isolate. Thus, an isolate selected for activating the antigen responsive cells will desirably elicit a cytokine response characterized by a low IL-10:IL-12 ratio but high expression of IFN-$\gamma$.

Preferably, the ratio will be less than 30, more preferably less than 20, 15, 10, 5 and even 4.

The vaccine will typically comprise the selected bacterial isolate(s) in an amount of between about 5% to about 80% w/w of the vaccine composition. As will be appreciated, the number of each isolate in the vaccine will be such that an effective dosage will be delivered to the mammal for activation of the common mucosal system taking into account the proposed mode of delivery and nature of the vaccine (eg. powder, liquid, aerosol delivery etc). The dosage of the, or each, bacterial isolate administered will typically be in a range of from about $10^9$ to about $10^{12}$ cfu, and more preferably from about $10^{10}$ to about $10^{11}$ cfu, respectively. The optimum dosage of a selected bacterial isolate can be determined by administering different dosages of the isolate to different groups of test mammals, prior to subsequently infecting the animals in each group with the corresponding live bacterial pathogen, and determining the dosage level required to achieve satisfactory clearance of the pathogen as would be well understood by the skilled addressee.

The vaccine itself may be freeze-dried or lyophilized for later reconstitution utilizing a physiologically acceptable buffer or fluid. The vaccine can also contain one or more anti-caking agents, isotonic agents, preservatives such as thimerosal, stablizers such as amino acids and sugar moieties, sweetening agents such sucrose, lactose or saccharin, pH modifiers sodium hydroxide, hydrochloric acid, monosodium phosphate and/or disodium phosphate, a pharmaceutically acceptable carrier such as physiologically saline, suitable buffers, solvents, dispersion media and isotonic preparations. Use of such ingredients and media for pharmaceutically active substances and vaccines is well known in the art. Except insofar as any conventional media or agent is incompatible with the bacterial isolate(s), their use in vaccines of invention is specifically encompassed. Supplementary active agents such as one or more cytokines for boosting the immune response, particularly cytokines characteristic of a Th1 response such as IFN-γ, IL-12 and TNF-β, can also be incorporated in the vaccine if desired.

In addition, a vaccine embodied by the invention may also comprise one or more adjuvants. Suitable adjuvants, pharmaceutically acceptable carriers and combinations of ingredients useful in vaccine compositions of the present invention may for instance be found in handbooks and texts well known to the skilled addressee such as "Remington" The Science and Practice of Pharmacy (Mack Publishing Co., 1995)", the contents of which is incorporated herein in its entirety by reference.

The oral killed bacterial vaccine may be administered as a dry powder or in liquid form. Administration can for example be achieved by aerosol inhalation, as a dosed liquid, by instillation, or as a spray. Devices for facilitating for delivery of oral vaccines are well known in the art and include metered dose inhalers (MDIs), dry powder inhalers (DPIs) and nebulisers including those which use ultrasonic energy or compressed air or other propellant to achieve atomisation. Propellants which may be used in MDIs include for instance chlorofluorocarbons (CFCs) such as trichlorofluorocarbon (CFC-11) and dichlorodifluorocarbon (CFC-12) and hydrofluoroalkanes.

In order that the nature of the present invention may be more clearly understood, preferred forms thereof will now be described with reference to the following non-limiting examples.

Example 1

Variation in T-Lymphocyte Activation Following Oral Immunization with Killed *P. aeruginosa* Oral Vaccine A study was conducted to demonstrate the variability in the capacity of recipient T cells to recognize and respond to an unselected isolate of killed bacteria. A cohort of nine human subjects with bronchiectasis were given two courses of killed oral *P. aeruginosa* (Ps.a) vaccine. Each course comprised administering two tables (each tablet containing $10^{11}$ killed bacteria) per day for three days, with the second course commencing on day 28. The *P. aeruginosa* isolate used was not selected other than being shown to be capable of activating the common mucosal system in an animal model.

Peripheral blood mononuclear cells were used as a source of antigen-primed T cells and were isolated from heparinized blood on a Ficoll/Paque density gradient. After centrifugation at 200 g for 20 mins at 4° C., the cells were collected from the plasma:ficoll interface, washed twice with PBS pH 7.4 and then resuspended at $2 \times 20^6$ cells/mL in AIM-V medium containing penicillin (100 U/mL), streptomycin (100 μg/mL) and 2-mercaptoethanol ($5 \times 10^{-5}$M). Cells were culture in wells of a 96-well flat-bottomed microtiter plate with or without Ps antigen (1 μg/mL) or PHA-P (2 μg/mL) in a total volume of 200 μL of AIM-V medium. After incubation for 4 days at 37° C. in a $CO_2$ incubator, the cultures were pulsed with 0.5 μCi per well of $^3$H-thymidine for the final 8 hrs before harvesting on a glass fibre filter using a cell harvester. After drying, the filters were counted in a scintillation counter. The results were expressed as mean cpm±SE.

Table 1 shows the post oral immunization mean counts ($H^3$-thymidine uptake representing antigen-induced proliferation) and the standard errors (SE's) of the means (representing the variation in individual responses).

TABLE 1

| T cell Ps. a antigen induced proliferation in humans | | | | |
|---|---|---|---|---|
| | PHA | | Ps. aeruginosa antigen (1 ug/ml) | |
| DAY | CPM × 00 | SE (as % of mean) | CPM × 000 | SE (as % of mean) |
| 0 | 84 | 13 | 3 | 16.5 |
| 28 | 82 | 12 | 4.4 | 65 |
| 56 | 80 | 12.5 | 9.5 | 42 |

The results shows that a consistent mean stimulation was induced throughout the study by the classical non-specific T cell mitogent PHA, with a consistent and small standard error, reflecting relatively similar proliferative responses. With Ps.a antigen stimulation before oral immunization, the standard error (SE) is of the same order as that found with PHA. However, at days 28 and 56 following oral immunization, a marked variation in response was noted (SE's of 64 and 42). These results show considerable variation in T cell responsiveness in vivo reflecting failure to select an isolate to engage the T cell receptor of most of the recipients.

As a control, DA rats (four per group) were orally immunized using the same isolate of Ps.a. Briefly, rats were given $5 \times 10^8$ paraformaldehyde killed *Pseudomonas aeruginosa* in PBS daily for 5 days per week for 2 weeks. Peripheral blood cells were isolated and $^3$H-thymidine uptake assessed as described above. The results are shown in Table 2.

TABLE 2

T cell Ps. a antigen induced proliferation in in-bred rats

|  | H³-thymidine CPM (×000) | SE (×000) (as % of mean) |
|---|---|---|
| Unimmunised | 16 | 19 |
| Immunised (tablet) | 35 | 13 |

A low SE of 13 was found in the in-bred DA rats (ie reflecting low genetic variability). It is concluded that the large SE (ie. reflecting degree of individual variation) in the human response is mainly due to variation in engagement of the antigen-presenting cell T-lymphocyte unit by the unselected vaccine candidate. This variation correlates with large differences in the level of protection observed between individuals in the human study, reflected by the high level of variation in the reduction in bacterial colonization (measured by numbers of bacteria in sputum) and in sputum purulence (measured as total white cell count) as determined at day 31. Specifically, bacteria counts were reduced in three subjects (1, 3.0, 1.0 log), remained unchanged in five subjects, and increased (2 logs) in one subject. The sputum white cell count fell with a mean of 40% reduction with a SE of 50%. Hence, the activation of T cells (which are responsible for white cell recruitment into the bronchus lumen with subsequent bacterial clearance, eg. see Dunkley et al (1994) 'A role for CD4+ T cells from orally immunized rats in enhanced clearance of *P. aeruginosa* from the lung. *Immunol* 83, 362-369) is also variable, indicating that the killed bacterial isolate utilized is not an optimal isolate for use as an oral killed bacterial vaccine in the general human population.

Example 2

Selection of an Optimal Isolate for Eliciting the Release of Cytokines

*S. aureus* and non-typeable *H. influenzae* isolates obtained from normal human subjects were killed by treatment with 2% paraformaldehyde in phosphate buffered saline (PBS). After incubation at room temperature for 1 hr, the treated bacteria were exhaustively washed in PBS and then tested for viability by culturing on mannitol salt agar or horse blood agar plates. The killed bacteria were adjusted to $2 \times 10^9$ cfu/mL by interpolation from a standard regression curve for Absorbance versus CFU. For use in culture stimulation, the bacteria from each isolate were adjusted to a final concentration of $2 \times 10^8$ CFU per ml in serum-free AIM-V medium containing penicillin (100 U/mL), streptomycin (100 µg/ml) and 2-mercaptoethanol (2-ME, $5 \times 10^{-5}$ M).

For *S. aureus* isolates, groups of male BALB/c mice (n=5) were given $5 \times 10^9$ killed whole cell bacteria by intragastric administration every 2 days per week for 2 weeks before challenge with live *S. aureus* bacteria administered intranasally. The dose was determined on the basis similar studies examining variable oral dosage. Control mice (n=5) were fed PBS alone. Reduction in colonization in the nose was determined at 24-48 hrs after challenge. For the NTHi isolates, groups of male BALB/c mice were given $5 \times 10^9$ killed whole cell bacteria by the intragastric route every 2 days per week for 2 weeks followed by intranasal challenge with live NTHi bacteria. Control mice were again fed PBS alone. Reduction in NTHi colonization was determined in bronchoalveolar washings (BAL) and lung homogenates, at 4 hrs following live challenge.

Human peripheral blood mononuclear cells (PBMNC) were separated from heparinized blood by centrifugation on a Ficoll/Paque density gradient. After washing by centrifugation, PBMNC were cultured in AIM-V medium at $2 \times 10^5$ cells per well with $2 \times 10^6$/ml or $2 \times 10^8$/ml CFU of killed bacteria in a total volume of 300 uL in wells of a 96-well flat-bottomed microtitre plate. After incubation at 37° C. and 5% $CO_2$ in air for 3 days, the culture supernatants were collected and stored at −20° C. until assay for cytokines by ELISA.

The capacity of individual *S. aureus* and NTHi isolates to stimulate cytokine production was tested using an antigen-presenting cell-T cell culture system. Briefly, PBMNC ($2 \times 10^6$/ml) containing APC and T cells were stimulated with graded doses of killed bacteria in flat-bottomed wells of a 96-well plate for 3 days at 37° C. in a $CO_2$ incubator. The culture supernatants were collected and assayed for IL-12 and IFN-γ by ELISA.

Table 3 shows the results of *S. aureus* isolates (A2, A3, A8, A15, A28, A19, A20) tested for their capacity to stimulate the production of IL-12 and IFN-γ. The results are medians normalized and expressed as a percentage of control. Variable stimulation of IL-12 and IFN-γ was observed. Isolates A2, A8, A28 and A19 were greater stimulators of both IL-12 and IFN-γ production than isolates A15, A20 and A3. Compared with the other isolates, stimulation with isolate A28 led to a 4-10 fold production of IL-12 and/or IFN-γ.

TABLE 3

Production of IL-12 and IFN-γ in cultures of peripheral blood mononuclear cells stimulated with different doses of killed whole cell *S. aureus* isolate.

|  | IL-12 pg/mL | | IFN-γ pg/mL | |
|---|---|---|---|---|
| Isolates | *10⁶ bacteria/l | *10⁸ bacteria/l | 10⁶ bacteria/l | 10⁸ bacteria/l |
| A2 | 147 | 186.5 | 2159 | 891.9 |
| A3 | <10 | <10 | 2242 | 2009 |
| A8 | 36.5 | 119 | 1938 | 1711 |
| A15 | <10 | <10 | <10 | 2476 |
| A28 | 1568 | <10 | 8592 | 9202 |
| A19 | 149.3 | 267.8 | 800.6 | 607.4 |
| A20 | 18.6 | 26.7 | 977.9 | 668.3 |

*numbers of killed bacteria per ml

When isolates A2, A8 and A28 were tested in cultures using PBMNC from 5 normal healthy subjects, only isolates A2 and A28 were capable of stimulating substantial amounts of IL-12 and IFN-γ in all subjects (Table 4 and Table 5). These results indicate that isolates A2 and A28 are potent stimulators of immunomodulating cytokines and, therefore, suitable as candidate immunostimulators, likely to mediate protective mucosal immunity in most recipients.

TABLE 4

Production of IL-12 in cultures of human peripheral blood mononuclear cells from normal healthy subjects stimulated with killed whole cell *S. aureus* isolate

|  | IL-12 (pg/mL) | | | | | | | | | |
|---|---|---|---|---|---|---|---|---|---|---|
| Iso- | Subject 1 | | Subject 2 | | Subject 3 | | Subject 3 | | Subject 5 | |
| lates | *10⁶ | *10⁸ | 10⁶ | 10⁸ | 10⁶ | 10⁸ | 10⁶ | 10⁸ | 10⁶ | 10⁸ |
| A2 | 138.6 | 193.7 | 11.3 | 147.5 | <10 | 87.6 | nd | 264.8 | nd | 271.8 |
| A8 | 157 | <10 | 46 | 10.6 | 27.6 | 29.7 | nd | nd | nd | nd |
| A28 | 112 | 214.2 | <10 | 137.2 | nd | 56.9 | nd | 328.2 | nd | 454.2 |
| None | — | <10 | — | <10 | — | <10 | — | <10 | — | <10 |

*number of killed bacteria per mL
nd = not determined

TABLE 5

IFN-γ production stimulated with killed whole cell *S aureus* isolate in cultures of human peripheral blood mononuclear cells from normal healthy subjects

| | IFN-γ (pg/mL) | | | | | | | | | |
|---|---|---|---|---|---|---|---|---|---|---|
| | Subject 1 | | Subject 2 | | Subject 3 | | Subject 3 | | Subject 5 | |
| Isolates | *$10^6$ | *$10^8$ | $10^6$ | $10^8$ | $10^6$ | $10^8$ | $10^6$ | $10^8$ | $10^6$ | $10^8$ |
| A2 | 1745 | 5501 | 3316 | 8689 | 963 | 8838 | nd | 12152 | nd | 6232 |
| A8 | 3388 | 4628 | 7458 | 7458 | 6479 | 8285 | nd | 11770 | Nd | nd |
| A28 | 724 | 5368 | 8547 | 1032 | 646 | 8429 | nd | 13560 | Nd | 6544 |
| None | — | <10 | — | <10 | — | <10 | — | <10 | — | <10 |

*numbers of killed bacteria per ml
nd = not determined

All NTHi isolates tested (B3, B4, B6, B10 and B14) were found capable of stimulating production of IL-12 and IFN-γ in variable amounts irrespective of the doses of bacteria used in culture stimulation (Table 6). Isolates B3 and B6 stimulated the generation of higher amounts of IL-12 and IFN-γ compared to the other NTHi isolates. The results are medians expressed as a percentage of control.

TABLE 6

Production of IL-12 and IFN-γ in cultures of peripheral blood mononuclear cells (PBMNC) stimulated with killed whole cell non-typable *H. influenzae* isolate

| | IL-12 (pg/mL) | | | | IFN-γ (pg/mL) | | | |
|---|---|---|---|---|---|---|---|---|
| Bacterial | $10^6$ bact./ml | | $10^8$ bact./ml | | $10^6$ bact./ml | | $10^8$ bact./ml | |
| Isolates | *PC | *RC | PC | RC | PC | RC | PC | RC |
| B3 | 65.5 | 20 | 42.8 | 20.6 | 1740 | 316 | 1723 | 786 |
| B4 | 25 | 13.2 | 18.2 | 14.8 | 956 | 76 | 1208 | 420 |
| B6 | 40.5 | 26.9 | 41.2 | 34.7 | 1755 | 436 | 2063 | 1758 |
| B10 | 18.2 | 16.2 | 24.4 | 21.2 | 378 | 53 | 1002 | 619 |
| B14 | 28.6 | 17.1 | 18.2 | 16.8 | 274 | 45 | 1341 | 713 |
| None | 23 | — | — | — | 19 | — | — | — |

*PBMNC from normal healthy subjects

Example 3

Selection of an Optimal Isolate of Bacteria as an Immunostimulator to Reduce Mucosal Colonization Two mouse mucosal colonization models were used to determine (1) the reduction in colonization of *S. aureus* in the nasal cavities and (2) the reduction in colonization of non-typeable *H. influenzae* in the lungs following challenge with live bacteria.

In model 1, 8 week old male SPF BALB/c mice (n=5) were given killed whole cell *S. aureus* bacteria ($5 \times 10^9$ per mouse) in 300 ul PBS by the intragastric route every 2 days per week for 2 weeks. Control mice received PBS alone. Paraformaldehyde-killed bacteria from isolates A2, A28, A3, A15, A19 and A20 were tested including an ATCC strain as a reference (ATCC 49247), respectively. One day after the final dose, mice were challenged with live *S. aureus* by administering 10 μl of $5 \times 10^9$ bacteria/ml into each nostril. At 24-48 hrs after challenge, mice were sacrificed and the nasal tissues excised. The tissues were homogenized in PBS and the homogenates collected then assayed for bacteria concentration by plating 10-fold serial dilutions of the homogenates on mannitol salt agar plates. CFU counts were determined after 24 hr incubation at 37° C.

Figure 2:
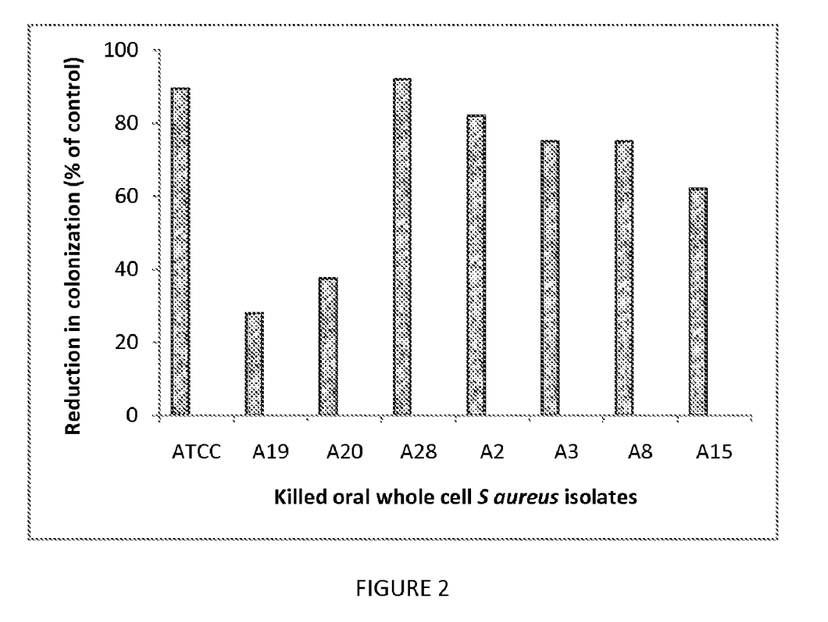
FIG. 2 is a graph showing reduction of S. aureus colonization in the nose of BALB/c mice by different whole cell killed isolates of the bacteria administered orally.

FIG. 2 shows that mice receiving killed bacteria prepared from isolates A19, A20, A28, A2, A3, A8 and A15 had reduced in compared with controls. The levels of protection were dependent on the isolates chosen with effectiveness being A28>A2>A8>A3>A15>A20>A19. Furthermore, the high levels of protection achieved with A28, A2 and A8 isolates correlated with their capacity to stimulate high levels of IL-12 and IFN-γ in cultures of human PBMNC (see Tables 3 and 4).

Figure 1:
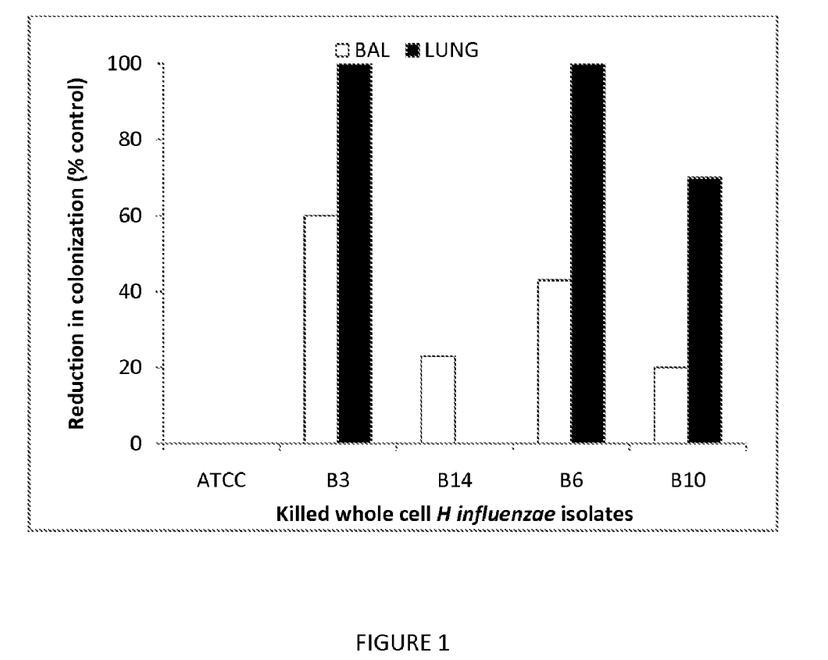
FIG. 1 is a graph showing reduction of NTHi colonization in the respiratory tract of BALB/c mice by different whole cell killed isolates of the bacteria administered orally.

In model 2, mice (n=5) were given killed whole cell NTHi ($5 \times 10^9$ per mouse) in 300 ul of PBS by the intragastric route every 2 days per week for 2 weeks before challenge with 10 ul of live bacteria in PBS ($5 \times 10^9$ per ml) administered by the intranasal route. Paraformaldehye-killed bacteria prepared from isolates B3, B14, B16 and B10 were tested, respectively. At 4 hrs following live challenge, the reduction in colonization in terms of bacterial clearance was determined in broncho-alveolar lavage fluid (BAL) and lung homogenates from treated and control mice. As shown in FIG. 1, of the isolates tested, B3, B16 and B10 gave the best clearance rate compared to the ATCC reference strain and isolate B14. When compared for in vitro stimulation of IL-12 and IFN-γ production, B3 and B6 isolates gave the best correlation with reduction in colonization (see Table 4).

Example 4

Selection of an Optimal Isolate of Bacteria as a Candidate Vaccine on the Basis of Optimal Cytokine Response In Vitro and Protection In Vivo Peripheral blood mononuclear cells (PBMNC) were separated from heparinized blood from normal healthy subjects by centrifugation on Ficoll/Paque density solution. The cells were collected from the plasma/ficoll interface and washed three times in PBS by centrifugation at 200 g for 15 mins at 4° C. Before culture, the cells were re-suspended in AIM-V serum-free medium at $2 \times 10^6$ cells/mL and the viability determined by trypan-blue exclusion test. One hundred microliter aliquots of the cell suspension were added in duplicates to equal volumes of AIM-V medium containing graded concentrations of killed bacteria or medium alone in wells of a flat-bottomed 96-well microtitre plate. The cultures were incubated for 3 days at 37° C. in an incubator with 5% $CO_2$ in air. After incubation, the supernatants were collected, pooled and stored at −20° C. until assay.

IL-10, IL-12 and IFN-γ in culture supernatants were measured by ELISA using monoclonal antibody pairs with recombinant proteins as standards. Briefly, wells of a flat-bottomed microtiter plate were coated with capture antibody overnight at 4° C. After washing, the wells were blocked with 2% BSA solution in PBS for 60 mins at room temperature (RT) and followed by washing in PBS/Tween. One hundred microliters of sample supernatant was added to each well. Following incubation for 90 mins at RT, the wells were washed and then 100 ul of biotinylated detector antibody was added. After incubation for 90 mins, HRP-conjugated streptavidin solution was added for 30 mins. The wells were then washed before adding TMB substrate solution for 20 mins. After colour development, the reaction was stopped with sulphuric solution before reading in an ELISA plate reader at 450 nm. The amount of cytokine secreted in culture supernatant was calculated by interpolation using the standard curve and the results were expressed as pg/mL.

Table 7 shows that high levels of IFN-γ and IL-12 produced by peripheral blood mononuclear cells stimulated with *S. aureus* (isolate A28) or NTHi (isolate B6) correlated with high levels of protection in the mouse model of colonization. In contrast, there was no correlation between isolates (A3 and B10) which stimulated low levels of cytokines and high levels of protection. Conversely, no correlation was observed between isolates (A19 and B14) which stimulated high levels of cytokines and low levels of protection. The results demonstrate that optimal cytokine response and in vivo protection are markers for the selection of an optimal isolate of bacteria as a candidate oral vaccine or immunostimulator to enhance mucosal immunity and reduce colonization in the airways.

TABLE 7

Correlation of in vitro cytokine production with in vivo bacterial clearance.

| Isolate | IL-12 (pg/mL) | IFN γ (pg/mL) | Protection (%) |
|---------|---------------|---------------|----------------|
| A28     | 1568          | 9202          | 91.3           |
| A3      | <10           | <10           | 74.7           |
| A19     | 267.8         | 800.6         | 28             |
| B6      | 412           | 1063          | 100            |
| B10     | <10           | 335           | 72.2           |
| B14     | 24            | 1341          | 24             |

Example 5

Selection of an Optimal Isolate Based on Differential Production of IL-10 and IL-12, and the Capacity to Enhance IFN-γ Production and Protection In Vivo Stimulation of PBMNC in culture by different isolates produced different amounts of IL-10 and IL-12 whose ratios correlated with the levels of IFN-γ and in vivo protection. As shown in Table 8, NTHi isolates (B3, B6) with a low IL-10/IL-12 ratio were better stimulators of a Th1 response characterized by maximal production of IFN-γ and decreased colonization of bacteria in the airways of mice orally immunized with killed vaccine isolates compared with controls. Conversely, isolates (B4, B10 and B14) with high IL-10/IL-12 ratios correlated with lower production of IFN-γ and higher levels of colonization. This was also true for *S. aureus* isolates where high levels of IFN-γ correlated with low IL-10/IL-12 ratios and low rates of colonization (Table 9). Taken together, the results show that an optimal isolate of bacteria can be selected as a candidate vaccine on the basis of low IL-10/IL-12 ratio and high IFN-γ and an enhanced protection in vivo. Thus, on the basis of these results, an optimal isolate would be associated with a cut-off value of IL-10/IL-12 ratio of say <15 and high production of IFN-γ (786 pg/ml for NTHi and >500 pg/ml for *S. aureus*) for all healthy subjects tested (minimum of 3 subjects).

TABLE 8

Selection of non-typable *H influenzae* isolates based on IL-10/IL-12 ratio and IFN-γ production and protection in vivo

| NTHi Isolate | Subject 1 | | Subject 2 | | Subject 3 | | Bacteria Colonisation* % of Control |
|---|---|---|---|---|---|---|---|
| | IL-10/IL-12 Ratio | IFN-γ (pg/ml) | IL-10/IL-12 Ratio | IFN-γ (pg/ml) | IL-10/IL-12 Ratio | IFN-γ (pg/ml) | |
| B3      | 10.9 | 1010 | 2.0  | 1740 | 1.25 | 786  | 37  |
| B6      | 7    | 1645 | 2.5  | 2063 | 0.41 | 1758 | 55  |
| B4      | 23.8 | 532  | 26.4 | 956  | 6.7  | 76   | 100 |
| B10     | 720  | 236  | 16.8 | 690  | 80   | 53   | 100 |
| B14     | 749  | 45   | 22   | 897  | 29.8 | 45   | 76  |
| Control | 51   | 0    | 10   | 23   | 1.24 | 19   | 100 |

*Colonisation rate in the airways of mice (n = 10) orally immunised with killed whole cell bacteria isolate or mice given PBS only (Control)

TABLE 9

Selection of *S. aureus* isolates based on IL-10/IL-12 ratio and IFN-γ production and protection in vivo

| S.aureus Isolate | Subject 1 | | Subject 2 | | Subject 3 | | Bacteria Colonisation* % of Control |
|---|---|---|---|---|---|---|---|
| | IL-10/IL-12 Ratio | IFN-γ (pg/ml) | IL-10/IL-12 Ratio | IFN-γ (pg/ml) | IL-10/IL-12 Ratio | IFN-γ (pg/ml) | |
| A2  | 0.99 | 5501 | 2.5  | 8639 | 5.9  | 8839 | 9.7  |
| A8  | 3.75 | 4623 | 13.2 | 7620 | 10.3 | 8250 | 26.2 |
| A28 | 1.6  | 5638 | 4.9  | 8547 | 14.3 | 8429 | 8.7  |
| A19 | 24   | 197  | 3.9  | 607  | 20.9 | 714  | 72   |

TABLE 9-continued

Selection of *S. aureus* isolates based on IL-10/IL-12 ratio
and IFN-γ production and protection in vivo

| S.aureus Isolate | Subject 1 | | Subject 2 | | Subject 3 | | Bacteria Colonisation* % of Control |
|---|---|---|---|---|---|---|---|
| | IL-10/ IL-12 Ratio | IFN-γ (pg/ml) | IL-10/ IL-12 Ratio | IFN-γ (pg/ml) | IL-10/ IL-12 Ratio | IFN-γ (pg/ml) | |
| A20 | 18 | 222 | 38.8 | 668 | 125.3 | 1075 | 62.5 |
| Control | 2 | 9.8 | 2 | 198 | 2.3 | 230 | 100 |

*Colonisation rate in the noses of mice (n = 10) orally immunised with killed whole cell bacteria isolate or mice given PBS only (Control)

Example 6

Stimulation of Peripheral Blood Mononuclear Cells by Non-Typeable *H. influenzae* Isolate NTHi 164

Whole killed NTHi 164 was cultured with PBMNC from normal healthy controls and IFN-γ production assessed. The results are shown in Table 10.

TABLE 10

Stimulation of IFN-γ production in PBMNC
stimulated with whole killed NTHi 164 isolate

| Whole killed NTHi 164 | Subject | | | |
|---|---|---|---|---|
| | MD | PH | PC | RC |
| | | IFN-γ (pg/ml) | | |
| $10^6$ bacteria/mL | 207 | 257 | 491 | 72 |
| $10^8$ bacteria/mL | 1738 | 1193 | 4533 | 514 |

Compared to Table 6 in Example 2, NTHi 164 expressed comparable levels of IFNγ for RC and higher level for PC than elicited by NTHi isolates B3 or B6. A particulate fraction of the NTHi isolate was also prepared and the capacity of the fraction to stimulate IFN-γ production assessed. The results are shown in Table 11. Briefly, NTHi 164 was revived from −80° C. storage onto chocolate agar plates then subcultured on chocolate agar. The bacteria were harvested, pelleted, washed and resuspended to 1010/ml in PBS. The suspension was sonicated at an amplitude of 6μ using 10 cycles of 30 seconds on and 60 seconds off. The suspension was centrifuged at 7000 g and the supernatant collected, sterile filtered, and protein content determined by Pierce BCA protein assay. Aliquots were stored frozen at −20° C. until use.

TABLE 11

Stimulation of IFN-γ production in PBMNC particulate
antigen of whole killed NTHi 164 isolate

| NTHi 164 antigen | Subject | | | | | | |
|---|---|---|---|---|---|---|---|
| | 1 | 2 | 3 | 4 | 5 | 6 | 7 |
| | | | | IFN-γ (pg/ml) | | | |
| 1 μg/mL | 130 | 287 | 24 | 111 | 156 | 86 | 35 |
| 10 μg/mL | 368 | 128 | 101 | 169 | 356 | 565 | 334 |

Tables 10 and 11 show that both whole killed NTHi 164 and the particulate antigen extract of the isolate stimulates peripheral blood mononuclear cells to produce IFN-γ. The production of IFN-γ is IL-12 dependent.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

REFERENCES

1. Dunkley et al, *Immunol.* (1994) 83, Pp. 362-369
2. Remington. "The Science and Practice of Pharmacy." (Mack Publishing Co., 1995)

The invention claimed is:

1. A method for selecting at least one microbial isolate for use in an oral killed vaccine against abnormal microbial colonization of a mucosal surface, of the selected microbial isolate or isolates, the method comprising:
    evaluating capacity of a plurality of different isolates of a unicellular microbe to activate antigen responsive cells to provide activation data for each microbial isolate;
    evaluating effectiveness of the isolates in reducing infection of a mucosal surface by the microbe to provide clearance data for each microbial isolate; and
    selecting at least one isolate from the microbial isolates, the activation data and clearance data for which correlate and is optimal for generating mucosal immunity against the microbe compared to the, or each, other of the isolates, or an isolate the activation data for which is optimal and a further isolate the clearance data for which is optimal, compared to the, or each, other of the isolates, respectively, for use in formulating the vaccine.

2. A method according to claim 1 wherein the microbial isolates are killed microbial isolates.

3. A method according to claim 1 wherein an isolate for which both the activation data and the clearance data is optimal compared to the other of the isolates is selected.

4. A method according to claim 1 wherein an isolate for which the activation data is optimal and a further isolate for which the clearance data is optimal, compared to the, or each, other of the isolates, are selected.

5. A method according to claim 1 wherein the mucosal immunity predominantly comprises a cellular immune response.

6. A method according to claim 1 wherein the activation data comprises antigen presenting cell data indicative of capacity to activate antigen presenting cells and data indicative of capacity to activate T-lymphocytes, and wherein the antigen presenting cell data and the T-lymphocyte activation data correlate.

7. A method according to claim 6 wherein the antigen presenting cell data comprises data indicative of capacity to induce IL-12 expression by the antigen responsive cells.

8. A method according to claim 7 wherein the antigen presenting cell data comprises data indicative of IL-12 expression relative to expression of IL-10 by the antigen responsive cells.

9. A method according to claim 8 wherein an isolate the activation data for which is indicative of capacity to elicit a cytokine response characterized by an IL-10:IL-12 ratio of about 30 or less is selected for use in the vaccine.

10. A method according to claim 6 wherein the further data comprises data indicative of capacity to induce IFN-γ expression by the antigen responsive cells.

11. A method according to claim 1 wherein the microbe is selected from the group consisting of bacteria, yeast or fungi.

12. A method according to claim 11 wherein the microbe is selected from microbial species selected from the group consisting of *Chlamydia* species, *Haemophilus* species, Non-typeable *Haemophilus* species, *Pseudomonas* species, *Streptococcus* species, *Staphylococcus* species, *E. coli* species, *Mycoplasma* species, *Helicobacter* species, *Candida* species and *Saccharomyces* species.

13. A method according to claim 12 wherein the microbe is selected from Non-typeable *H. influenzae, S. aureus, P. aeruginosa* and *S. pneumoniae*.

14. A method for providing an oral killed vaccine against abnormal microbial colonization of a mucosal surface, of at least one selected microbial isolate the method comprising:
evaluating capacity of a plurality of different isolates of a unicellular microbe to activate antigen responsive cells to provide activation data for each microbial isolate;
evaluating effectiveness of the isolates in reducing infection of a mucosal surface by the microbe to provide clearance data for each microbial isolate;
selecting at least one isolate from the plurality of isolates, the activation data and clearance data for which correlate and is optimal for generating mucosal immunity against the microbe compared to the, or each, other of the isolates, or an isolate the activation data for which is optimal and a further isolate the clearance data for which is optimal, compared to the, or each, other of the microbial isolates, respectively, for use in formulating the vaccine; and
wherein the vaccine is formulated by mixing the selected isolate or isolates with one or more pharmaceutically acceptable excipients suitable for oral administration.

15. A method according to claim 14 wherein the microbial isolates are killed microbial isolates.

16. A method according to claim 14 wherein an isolate for which both the activation data and the clearance data is optimal compared to the, or each, other of the isolates is selected.

17. A method according to claim 14 wherein an isolate for which the activation data is optimal and a further isolate for which the clearance data is optimal, compared to the, or each, other of the isolates, are selected.

18. A method according to claim 14 wherein the mucosal immunity predominantly comprises a cellular immune response.

19. A method according to claim 14 wherein the antigen responsive cells comprise one or more cell types selected from the group consisting of antigen presenting cells and T-lymphocytes.

20. A method according to claim 19 wherein the antigen responsive cells comprise both antigen presenting cells and T-lymphocytes.

21. A method according to claim 20 wherein the antigen presenting cells comprise macrophages.

22. A method according to claim 20 wherein the T-lymphocytes are Th1 lymphocytes or Th1 committed T-lymphocytes.

23. A method according claim 14 wherein the activation data comprises antigen presenting cell data indicative of capacity to activate antigen presenting cells and data indicative of capacity to activate T-lymphocytes, and wherein the antigen presenting cell data and the T-lymphocyte activation data correlate.

24. A method according to claim 23 wherein the antigen presenting cell data comprises data indicative of capacity to induce IL-12 expression by the antigen responsive cells.

25. A method according to claim 24 wherein the antigen presenting cell data comprises data indicative of IL-12 expression relative to expression of IL-10 by the antigen responsive cells.

26. A method according to claim 25 wherein an isolate the activation data for which is indicative of capacity to elicit a cytokine response characterized by an IL-10:IL-12 ratio of about 30 or less is selected for use in the vaccine.

27. A method according to claim 23 wherein the T-lymphocyte activation data comprises data indicative of capacity to induce IFN-γ expression by the antigen responsive cells.

28. A method according to claim 14 wherein the effectiveness of the isolates to reduce infection of the mucosal surface is evaluated by determining capacity of the isolates to reduce the infection of the mucosal surface in vivo.

29. A method according to claim 14 wherein the microbe is selected from the group consisting of bacteria, yeast or fungi.

30. A method according to claim 29 wherein the microbe is selected from microbial species selected from the group consisting of *Chlamydia* species, *Haemophilus* species, Non-typeable *Haemophilus* species, *Pseudomonas* species, *Streptococcus* species, *Staphylococcus* species, *E. coli* species, *Mycoplasma* species, *Helicobacter* species, *Candida* species and *Saccharomyces* species.

31. A method according to claim 30 wherein the microbe is selected from Non-typeable *H. influenzae, S. aureus, P. aeruginosa* and *S. pneumoniae*.

32. A method for providing an oral killed vaccine against abnormal microbial colonization of a mucosal surface, of at least one selected microbial isolate the method comprising:
evaluating capacity of a plurality of different isolates of a unicellular microbe to induce expression of IL-10 and IL-12 in antigen responsive cells;
selecting at least one isolate from the microbial isolates, that induces optimal expression of IL-12 relative to IL-10 compared to the, or each, other of the isolates, respectively, for use in formulating the vaccine; and
wherein the vaccine is formulated by mixing the selected isolate or isolates with one or more pharmaceutically acceptable excipients suitable for oral administration.

33. A method according to claim 32 wherein the selected isolate induces expression of the IL-10 and IL-12 at a ratio of IL-10 to IL-12 of about 30 or less.

34. A method according to claim 33 wherein the ratio is about 15 or less.

35. A method according to claim 32 wherein the isolate further induces expression of IFN-γ by the antigen responsive cells.

36. A method according to claim 35 wherein the expression of IFN-γ by the isolate is optimal compared to the, or each, other of the isolates, respectively.

37. A method according to claim 32 wherein the antigen responsive cells comprise peripheral blood mononuclear cells.

38. A method according to claim 32 wherein the antigen responsive cells comprise antigen presenting cells and T-lymphocytes.

39. A method according to claim 32 wherein the microbe is selected from microbial species selected from the group consisting of *Chlamydia* species, *Haemophilus* species, Non-typeable *Haemophilus* species, *Pseudomonas* species, *Streptococcus* species, *Staphylococcus* species, *E. coli* species, *Mycoplasma* species, *Helicobacter* species, *Candida* species and *Saccharomyces* species.

40. A method according to claim 39 wherein the microbe is selected from Non-typeable *H. influenzae, S. aureus, P. aeruginosa* and *S. pneumoniae*.

41. An oral killed vaccine prepared by the method of claim 14.

42. An oral killed vaccine prepared by the method of claim 32.

* * * * *